(12) United States Patent
Alfano et al.

(10) Patent No.: US 8,518,445 B2
(45) Date of Patent: Aug. 27, 2013

(54) CHANGING SKIN-COLOR PERCEPTION USING QUANTUM AND OPTICAL PRINCIPLES IN COSMETIC PREPARATIONS

(75) Inventors: Robert R. Alfano, Bronx, NY (US); Xiaohui Ni, New York, NY (US); Manuel Zevallos, Woodhaven, NY (US)

(73) Assignee: Research Foundation of the City University of New York, New York, NY (US)

( * ) Notice: Subject to any disclaimer, the term of this patent is extended or adjusted under 35 U.S.C. 154(b) by 1521 days.

(21) Appl. No.: 11/656,738

(22) Filed: Jan. 22, 2007

(65) Prior Publication Data

US 2007/0274938 A1 Nov. 29, 2007

Related U.S. Application Data

(60) Provisional application No. 60/761,411, filed on Jan. 20, 2006.

(51) Int. Cl.
*A61K 9/14* (2006.01)

(52) U.S. Cl.
USPC .......................................... 424/489; 424/63

(58) Field of Classification Search
USPC .................................... 424/489, 63
See application file for complete search history.

(56) References Cited

U.S. PATENT DOCUMENTS

| | | | |
|---|---|---|---|
| 5,690,916 A * | 11/1997 | Kimura et al. | 424/59 |
| 5,980,904 A | 11/1999 | Leverett et al. | |
| 6,669,932 B2 | 12/2003 | Imanaka et al. | |
| 6,833,959 B2 | 12/2004 | Phillips et al. | |
| 6,913,830 B2 | 7/2005 | Decker et al. | |

OTHER PUBLICATIONS

Thomas Fuller, A Vision of Pale Beauty Carries Risks for Asia's Women, The new York Times, May 14, 2006, New York, USA.
Wolfgang Luther, Industrial Application of Nanomaterials—Chances and Risks, Aug. 2004, VDI Technologiezentrum, Dusseldorf, Germany.

* cited by examiner

*Primary Examiner* — Fereydoun G Sajjadi
*Assistant Examiner* — Danielle Sullivan
(74) *Attorney, Agent, or Firm* — Lackenbach Siegel, LLP; Myron Greenspan (57) ABSTRACT

The present invention teaches how to change the skin color perception, mainly the facial color from red, blue or yellow to white appearance, using quantum and optical principles. By selecting the right size and material of particles compounded in cosmetic preparations and applying the preparations to the skin, the scattering and/or emission from micro- and nano-particles can provide a complementary color or in proximity to that complementary color of the skin color. The mixture of the color provided by the particles and the reflected color from the skin will whiten the skin or make inconspicuous of the hyperchromic portion of the skin. The invention can also be used for other applications in which the particles can be applied to a surface or blended into a material, such as, for example, automobile paint, house paint, glass color and nail polish.

37 Claims, 13 Drawing Sheets

CHANGING SKIN-COLOR PERCEPTION USING QUANTUM AND OPTICAL PRINCIPLES IN COSMETIC PREPARATIONS

CROSS REFERENCE TO RELATED APPLICATION

This application is based on and claims priority of Provisional Patent Application Ser. No. 60/760,411 filed on Jan. 20, 2006.

BACKGROUND OF THE INVENTION

1. Field of the Invention

The present invention relates to changing the color of skin and other materials using the scattering, emission and absorption properties of nanoparticles. Techniques are disclosed for changing the appearance of skin color and making it whiter by removing the redness, blueness or yellowness appearance using particles of size from nanometer to micrometer.

2. Description of the Prior Art

Color is a property of the light that reaches our eyes. The light is emitted from materials in quantum process. The colors we see depend on the frequency (v) of the light we see. The transition energy is produced from a quantum process with energy $\Delta E = h\nu$. Different frequencies of visible light are perceived as different colors; the lowest frequency we detect appears to most people as the color red and the highest as violet. Between them range the infinite number of hues. Red (~620 nm), green (~530 nm) and blue (~440 nm) are called the primary colors. By an additive mixture of the primary colors, we can produce different colors in the spectrum. For example, by adding red, green and blue light together the resulting light appears white; and mixing of yellow with blue light gives white. The mixing of paints is an entirely different process from the mixing of colored lights. Paint is composed of pigments-tiny solid particles in scattering host that produce their characteristic colors by the processes of selective absorption or selective transmission of frequencies. The mixture of absorbing pigments results in a subtraction of colors; the observer sees the light left over after absorption taken place. The magenta, cyan, and yellow are called the subtractive primary colors. The pigments of these three colors can be combined to produce any color in the spectrum in painting or printing. When an additive primary and its opposite subtractive primary combine additively-green with magenta, for example, they produce white. Any two colors that add together to produce white are called complementary colors. As mentioned above, the addition of blue and yellow gives white, yellow is the complementary color of blue. Yellow clothes can be whiten by adding a blue emitting dye.

People of different descent have different skin colors, such as yellow for Asian and oriental people. Various medical conditions can also result in skin coloration such as blueness from cyanosis. People face skin problems as they age, like chronic redness called Rosacea. Our skin pigment changes significantly due to the aging effect of ultraviolet light exposure. This results in the formation of a sallow red color. Even though we may feel healthy, this pigment change often creates an unhealthy look. Skin color problems affect large group of people today. To maintain the youthful and healthy look of their face, men and women use cosmetic material daily. Skin color is primarily determined by the amount of melanin present in the skin. A reduction of the amount of melanin in the skin by cosmetic composition can whiten the skin. [U.S. Pat. No. 5,980,904 issued Nov. 9, 1999 to Jesse C. Leverett et al.] Alternatively, the white pigments or color pigments are compounded as cosmetic bases to form cosmetic product for covering skin discolorations and changing the skin appearance [U.S. Pat. No. 6,669,932 issued Dec. 30, 2003 to Imanaka et al.]. A skin-color adjusting method using material that transmits the complementary color of the skin color can make the hyperchromic portion naturally inconspicuous [U.S. Pat. No. 5,690,916 issued Nov. 25, 1997 to Kimura et al.] The prior arts also use multilayer interference film to shift skin color [U.S. Pat. No. 6,833,959 issued Dec. 21, 2004 to Phillips et al.]. Nanotechnology holds the promise for use in cosmetics. Nanoparticulate titania and zinc oxide are used for absorbing UV light in sunscreens. The colorants have been made with semiconductor particles which exhibit sized-quantized absorption of visible light [U.S. Pat. No. 6,913,830 issued Jul. 5, 2005 to Decker et al.].

This patent teaches the use of quantum processes from scattering, emission and/or absorption of radiation in the visible at key wavelengths to alter the appearance of facial color. Since scattering and emission properties of micro- and nanoparticles can alter the color distribution, method to apply the scattering, emission and/or absorption for skin color changing should be explored. We teach that adding scattering of blue light or emitting of blue light to yellow face results in white appearance of the face, adding blue and green light from scattering or emission to red face results in white appearance face.

SUMMARY OF THE INVENTION

The present invention teaches us to alter the skin color using the scattering, emission and absorption properties of micro- and nanoparticles. Both quantum and optical properties of materials (index of refraction) are considered. When white light illuminates a nanoparticle, the observer can see a color depending on the size as well as other parameters like the refractive index of the particle. The scattered color light mixed with the reflected light from the skin can give a white appearance for colored skin due to this additive mixture, changing yellow to white or red to white by using scattering and/or emission and/or absorption from micro- or nanoparticles. Scattering from particles in nanometer range gives rise to blue and green colors. Adding this to red gives white.

Emission from nanoparticle can also change the skin color by additive mixture. Semiconductor particle like quantum dots or fluorescent nanoparticles can absorb ultraviolet radiation and emit a complementary color for the skin color, the mixture of the emitted light with the reflected light from skin can make the skin white.

A pigment or metallic gold or silver (due to surface plasmons) of micro- or nanometer can absorb certain colors and transmit or reflect others. By mixing the transmitted or reflected colors with the reflected one from the skin we can obtain a white color of skin.

It is, therefore, an object of the present invention to provide methods for changing the appearance of the color skin to appear whiter. The method includes using scatterers, emitters or absorbers in cosmetic preparations.

Accordingly, an object of the present invention is to provide skin-whitening methods using the scattering, emission and absorption properties of micro- and nanoparticles. Quantum size effects are used to alter the skin color. Any facial color can be altered by adjusting distribution of light from scattering, emission and absorption of different colors.

It is a further object to also use the aforementioned method to add micro- and nanoparticles to other materials by applying these either to the surface or embedding them within the materials to change the color perception by such materials or surfaces thereof.

BRIEF DESCRIPTION OF THE DRAWINGS

The inventive method will now be described with reference to the annexed drawings, in which.

DESCRIPTION OF THE PREFERRED EMBODIMENT

Scattering is a universal phenomenon, in which small particles suspended in a medium of a different index of refraction diffuse a portion of the incident radiation in various directions. Light scattering theory may be categorized in three different types: Rayleigh scattering, Mie scattering, and non-selective scattering. The size of scattering particle(d) in comparison with the incident wavelength $\lambda$ is a key parameter. Rayleigh scattering occurs when the particles causing the scattering are much smaller in size than the wavelengths of the light. Rayleigh scattering is wavelength dependent. As the wavelength decreases, scattering increases as for small particles:

$$I = I_0 \frac{8\pi^4 N\alpha^2}{\lambda^4 R^2}(1+\cos^2\theta) \propto \frac{1}{\lambda^4} \quad (1)$$

The strong wavelength dependence of the scattering ($\sim\lambda^{-4}$) means the blue light is scattered much more strongly than the red light, this is the reason why the sky is blue.

When the wavelength is of the order of the scattering particle, interference effects dominate the scattering and scattering intensity is heavily dependent on the size and scattering angle. This scattering region is call Mie scattering. In the case of the size of the particle being much larger than the wavelength of incident light, the change in direction of the incident light can be explained by geometrical optics, such as diffraction, refraction, or a combination of these effects.

Scattering from small particles follows Mie scattering theory. As an exact solution to the scattering of a plane electromagnetic wave by a dielectric sphere, Mie scattering has no size limitations and may be used for describing most spherical particle systems, including Rayleigh scattering. Considering a light beam impinging on a spherical particle along a direction S, we choose a reference plane through the direction of propagation. The electric field vector is represented by:

$$\vec{E} = Re[E_l \vec{l} + E_r \vec{r}] \quad (2)$$

where $E_l = a_1 \exp(i\delta_1)$, the component parallel to the reference plane ($E_\parallel$), and $E_r = a_2 \exp(i\delta_2)$, the component perpendicular to the reference plane ($E_\perp$). The scattering of electric vector $E_l$, $E_r$ by a sphere can be described using amplitude function S. In the far-field zone (i.e., at the large distance r from a sphere), the solution of the vector wave equation can be obtained as $$\begin{bmatrix} E_l^s \\ E_r^s \end{bmatrix} = \frac{\exp(-ikr+ikz)}{ikr} \begin{bmatrix} S_2 & S_3 \\ S_4 & S_1 \end{bmatrix} \begin{bmatrix} E_l^i \\ E_r^i \end{bmatrix} \quad (3)$$

The scattering matrix describes the relation between incident and scattered electric field component perpendicular and parallel the scattering plane. The four amplitude function, $S_1$, $S_2$, $S_3$, and $S_4$, all functions of $\theta$ (scattering angle) and $\phi$ (azimuth angle), form the scattering matrix $S(\theta, \phi)$ of four element. It is a fundamental equation of scattered radiation including polarization in the far field.

For spheres, the non-diagonal scattering amplitude functions $S_3=S_4=0$. Thus, for spheres it reduces to $$\begin{bmatrix} E_l^s \\ E_r^s \end{bmatrix} = \frac{\exp(-ikr+ikz)}{ikr} \begin{bmatrix} S_2 & 0 \\ 0 & S_1 \end{bmatrix} \begin{bmatrix} E_l^i \\ E_r^i \end{bmatrix} \quad (4)$$

where $\exp(ikz)$ is the incident plane wave, and $$\frac{\exp(-ikr)}{ikr}$$

is the outgoing scattered wave.

The amplitude functions $S_1$ and $S_2$ depend only on the scattering angle $$S_1(\theta) = \sum_{n=1}^{\infty} \frac{2n+1}{n(n+1)} [a_n \pi_n(\cos\theta) + b_n \tau_n(\cos\theta)] \quad (5)$$

$$S_2(\theta) = \sum_{n=1}^{\infty} \frac{2n+1}{n(n+1)} [b_n \pi_n(\cos\theta) + a_n \tau_n(\cos\theta)] \quad (6)$$

where $\pi_n$ and $\tau_n$ are Mie angular functions $$\pi_n(\cos\theta) = \frac{1}{\sin(\theta)} P_n^1(\cos\theta) \quad (7)$$

$$\tau_n(\cos\theta) = \frac{d}{d\theta} P_n^1(\cos\theta) \quad (8)$$

where $P_n^1$ are the associated polynomials.

The coefficients $a_n$ are related to the amplitudes of the electric oscillations, while the coefficients $b_n$ are related to the amplitudes of the oscillations of a magnetic type.

$$a_n = \frac{m\psi_n(mx)\psi_n'(x) - \psi_n(x)\psi_n'(mx)}{m\psi_n(mx)\xi_n'(x) - \xi_n(x)\psi_n'(mx)} \quad (9)$$

$$b_n = \frac{m\psi_n(x)\psi_n'(mx) - \psi_n(mx)\psi_n'(x)}{m\xi_n(x)\psi_n'(mx) - \psi_n(mx)\xi_n'(x)} \quad (10)$$

where $x = ka = 2\pi a/\lambda$, a is the radius of the sphere, k is the propagation constant in free space, m is the refractive index of the sphere material relative to its surrounding medium. $\Psi$ and $\xi$ are defined as:

$$\psi_n(z) = z j_n(z) \text{ and } \xi_n(z) = z h_n^{(2)}(z)$$

where $j_n$ is the Bessel function and $h_n^{(2)}$ is the spherical Bessel function.

The scattering cross section $\sigma_s$ is given by $$\sigma_s = \frac{2\pi}{k^2} \sum_{n=1}^{\infty} (2n+1)(|a_n|^2 + |b_n|^2) \quad (11)$$

Eq. (2)-(11) provides an exact solution for light scattering from a small particle. Giving the particle size, refractive index and incident wavelength, we have calculated the scattered intensity at different scattering angle from Eq. (2)-(11) for different $\lambda$. The refractive index and size effects of the scattering of visible light can be easily evaluated from those equations.

Figure 1:
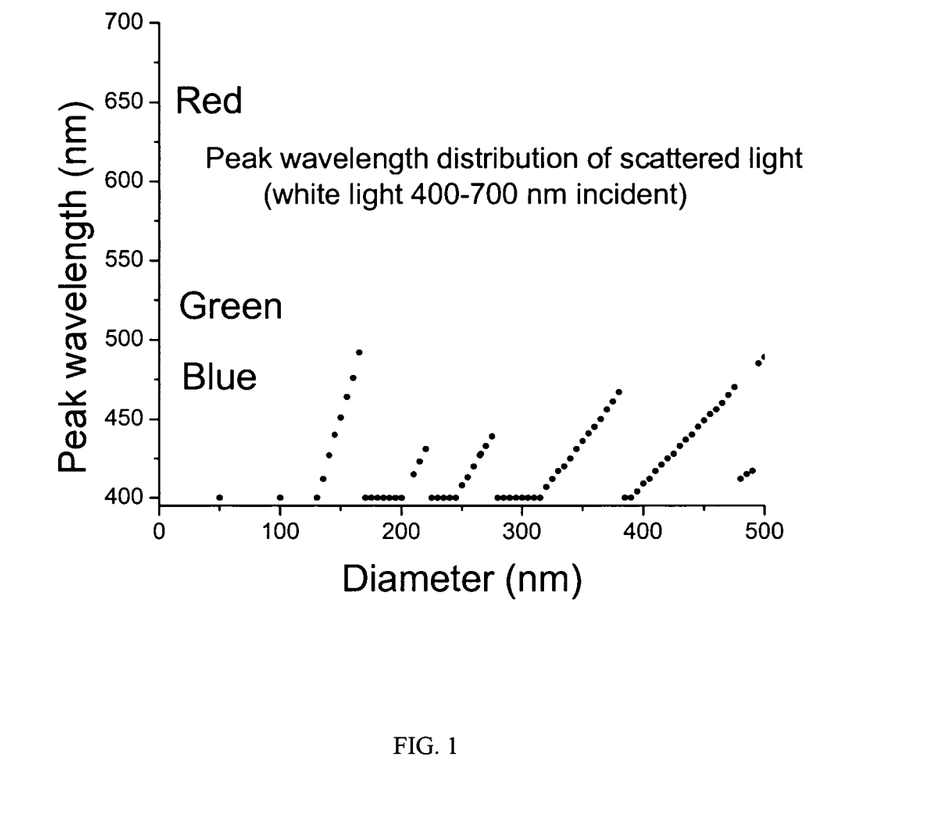
FIG. 1 is a curve calculated from Mie theory showing the peak wavelength of scattered light from ZnO for different particle sizes at the near backward scattering angle 136°. The particle is illuminated with white light of even intensity in the spectrum range 400 nm to 700 nm and gives more blue and green light depending on size.
Figure 2:
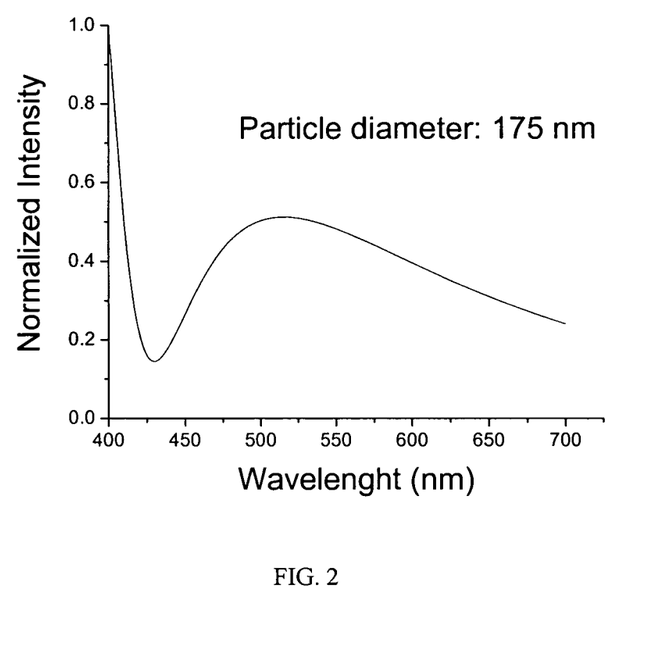
FIG. 2 shows the normalized intensity at the angle 136° (near backward) for even intensity light illuminating nanoparticles of diameter 175 nm.
Figure 3:
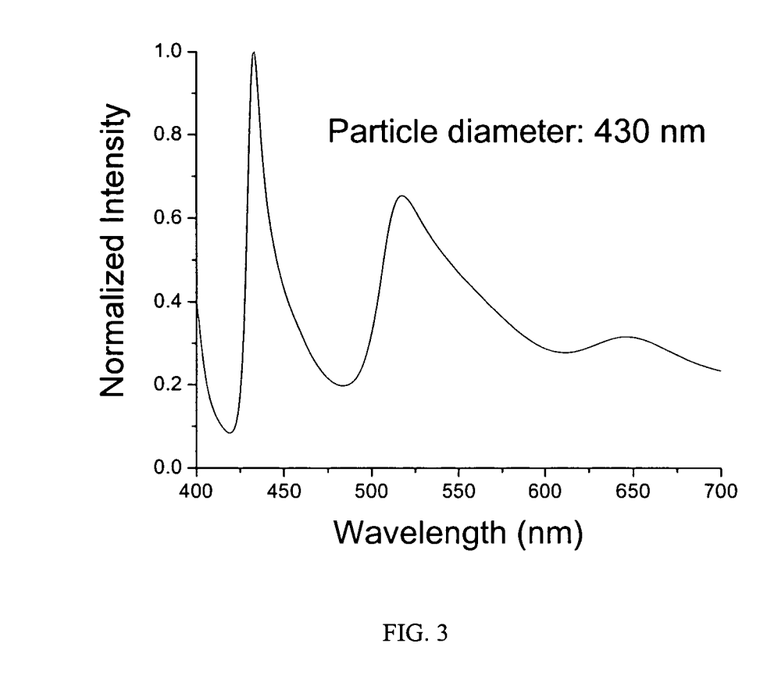
FIG. 3 shows the normalized intensity at the angle 136° (near backward) for even intensity light illuminating nanoparticles of diameter 430 nm.

FIG. 1 is the calculated peak wavelength via particle size at the scattering angle 136° using Mie theory for white light (even intensity of spectrum component from 400 nm to 700 nm) incident upon a Zinc Oxide (ZnO) colloidal sphere. FIG. 1 shows that the scattered light prefers the blue-green color for the particle size less than 500 nm. Actually, for particle diameter less than 130 nm, the shorter wavelengths are scattered most strongly, which so called Rayleigh scattering. With the increase of particle sizes from 100 nm to 500 nm, the scattering is dominated with Mie scattering and the peak wavelength is shifted between green and violet due to resonance effect. There is more than one peak in the wavelength range from 400 nm to 700 mm. FIG. 2 and FIG. 3 show the normalized intensity at the angle 136° (near backward) for even intensity light illuminating nanoparticles of diameter 175 nm and 430 nm, respectively. Beside the peak of violet light, there exists a peak of green light in FIG. 2. Since the spectrum of light emission from the sun is not constant at all wavelength and the retina in our eyes response most strongly to light at red, blue and green color, FIG. 2 gives a green color at the near backward angle for sunlight illumination. The existence of blue and green light peaks in FIG. 3 gives a cyan color (blue+green) for sunlight illumination.

For a larger particle than the wavelength mentioned above, we can also calculate the scattered color distribution. At that case, the distribution is more complicated and it is hard to get few clear peak wavelengths. The scattering from the large particles is dominated by forward scattering, the micro- or nanoparticles on the skin will have low opacity. The skin has less gloss with the large size of particles.

ZnO is commonly found in cosmetics as a whitening agent for the reason of high refractive index, which expressed the ability to scatter the light backward. There are some other white pigments like $TiO_2$ and MgO that are widely used as cosmetic materials. FIG. 1 has shown that sunlight backscattered from ZnO particle has preferred color depending on the diameter of ZnO sphere. The key of our teaching is the "correct" selection of the diameter of ZnO. We can obtain a complimentary color of the skin color. Mixture of backscattered light from the ZnO particle and the reflected light from the skin will turn the skin color to white appearance in color. The size distribution of particles is key for color scattering (see FIG. 1).

Figure 4:
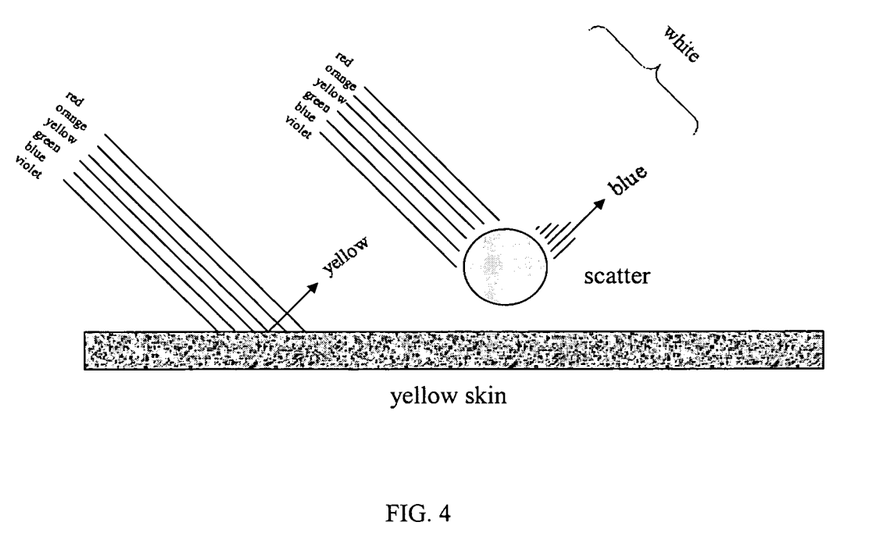
FIG. 4 is an enlarged view showing how the scattering from nanoparticles on the skin changes the skin color of yellow to white appearance in color.

FIG. 4 shows how the scattering from nanoparticles change the skin color of yellow to white appearance in color. As we can see from FIG. 1, backscattered light from ZnO particles with diameter around 160 nm, 350 nm or 480 nm is dominated with blue light at the wavelength of 475 nm. All colors beside the yellow one are absorbed by the yellow skin. The reflected yellow (red+green) light from the skin mixed with the scattered light blue light will give an appearance of white color.

Figure 5:
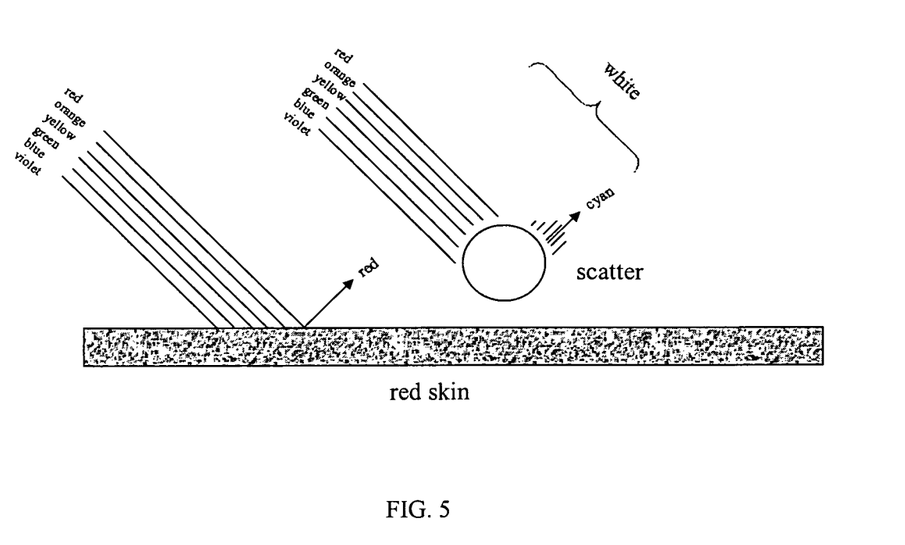
FIG. 5 is an enlarged view showing how the scattering from nanoparticles on the skin changes the skin color of red to white appearance in color.

FIG. 5 shows how the scattering from nanoparticles change the skin color of red to white appearance in color by using ZnO particles with diameter around 175 nm, where the cyan color (blue+green) is strongly scattered. The cyan color in the scattered light mixed with reflected red color from the skin gives a white appearance for red skin.

Semiconductor particles like quantum dots or Fluorescent nanoparticles can be excited by the short wavelength component in incident spectrum and emit light of longer wavelength. The peak emission wavelength of quantum dots is extreme sensitivity to both the dot composition and size due to the quantum confinement effect. When the size of a semiconductor crystal is on the scale of the material's exciton Bohr radius, the electron energy levels will be discrete rather than continuous in the bulk materials. Because the emission frequency of a dot depends on the energy levels, it is therefore possible to control the emission wavelength of a quantum dot by adjusting the size of the dot. The emission from quantum dots like CdSe, GaP, AlAs, InN, in P, AlSb, CdTe, ZnTe, BeTe or cell quantum dots like CdSe/ZnS, CdTe/CdS or alloys like ZnCdSe can cover the entire or partial visible range by changing the sizes. Quantum dots are commercially available in narrow emissions from 465 nm to 2300 nm (Evident Technologies).

Figure 6:
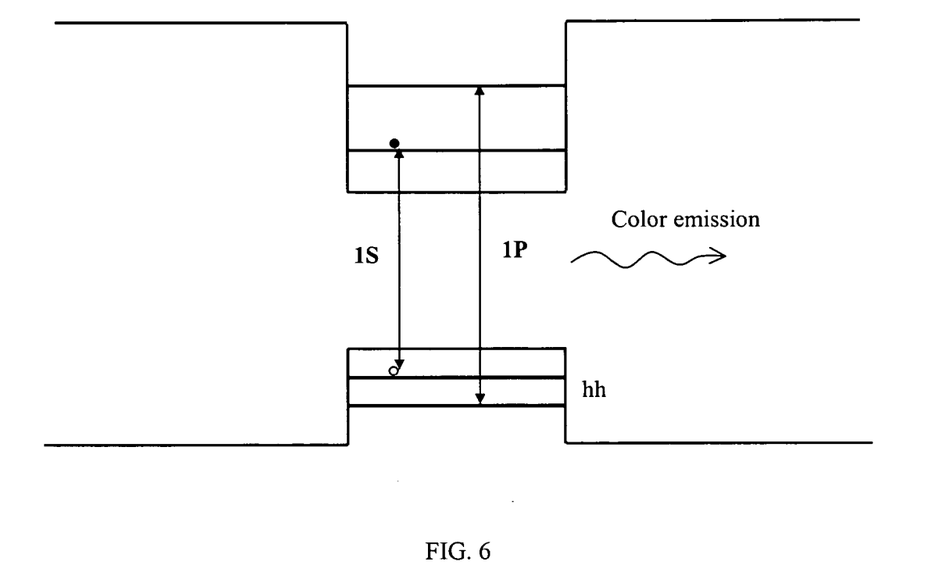
FIG. 6 shows the eigenenergies levels for electrons and holes in the CdSe quantum dot. Two vertical lines with arrows show 1S and 1P excitons.

FIG. 6 displays the eigenenergy states for both electron and hole in a CdSe quantum spherical dot with a radius $r_0$ in the intermediate confinement regime. The two vertical lines with arrows show 1S and 1P excitons. Under the effective-mass approximation, the eigenenergies of an electron confined in an infinite spherical well is given by $E_{n,l}=\hbar_{n,l}^2/2m_e r_0^2$, where n, l are radial and angular quantum numbers. The ground state and the first excited state are denoted as 1S [(n,l)=(1,0)] and 1P [(n,l)=(1,1)]. When an electron is in the l=0 state, the eigenenergies of hh (heavy hole) are described by $E_{1,0}^{n',l'}=-2.44e^2/\in r_0+\hbar\omega_1(2n'+l'+\frac{2}{3})$, where n' and l' have the same meaning as n and l but for hh, and $\omega_1=[(2\pi^2/3\ m_{hh}r_0^2)e^2/\in_0]^{1/2}$ with $m_{hh}=[m_{hh(l)}m_{hh(t)}^2]^{1/3}$. For given value of the radius of dot, the lowest hh excitonic transition energies are given by $$E_{1S}=E_g+E_{1,0}+E_{1,0}^{1,0} \quad (12)$$

$$E_{1P}=E_g+E_{1,1}+E_{1,1}^{1,1} \quad (13)$$

where $E_g$ is the bandgap of the bulk materials.

Figure 7:
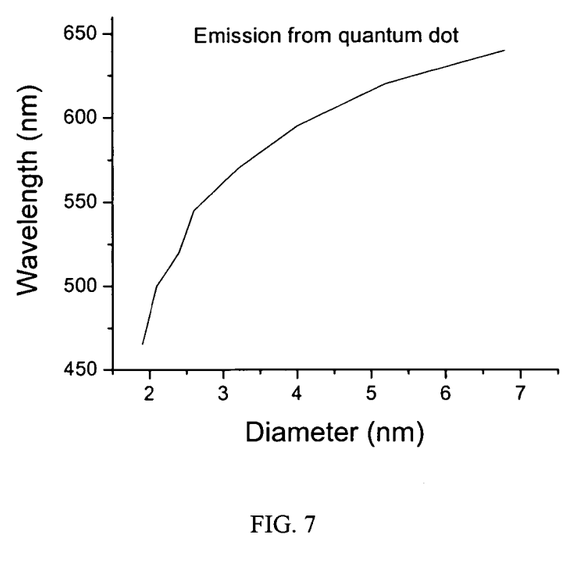
FIG. 7 is a curve showing the emission peak of different sizes of CdSe quantum dots from blue to red emission. One can use different sizes to get blue and red emission using a diameter of 6.8 and 1.9 nm quantum dot.

Eq. (12) and (13) give an expression of the transition energies. By adjusting the radius $r_0$ of the quantum dot, the transition energies, or emission wavelengths will be changed. FIG. 7 shows the size dependent emission of CdSe quantum dots from Evident Technologies. The emission peak is shifted from blue color (465 nm) to red color (640 nm) with the increase of particle diameter from 1.9 nm to 6.8 nm. This kind of size dependent emission together with composition dependent emission can be used to change the skin color.

Figure 8:
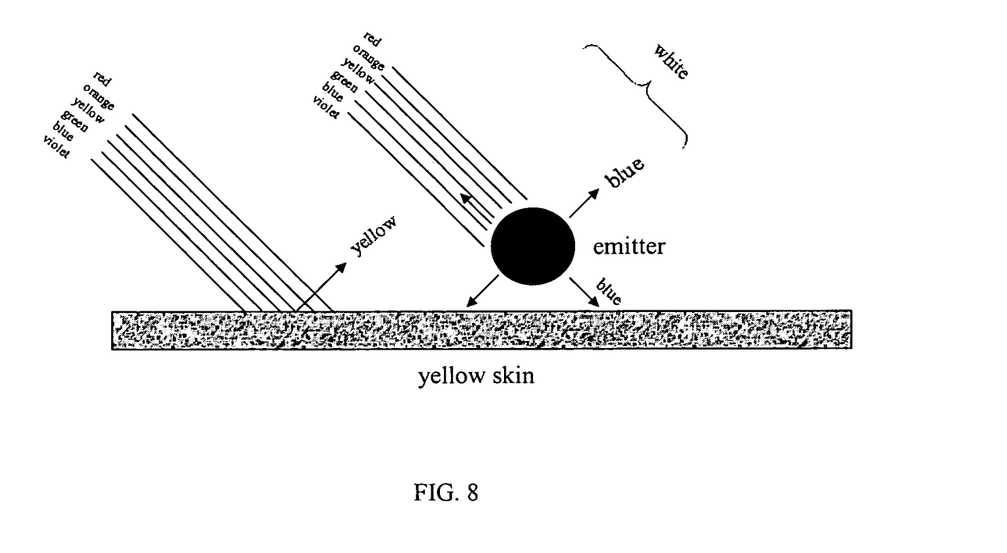
FIG. 8 is an enlarged view showing how a nanometer emitters changes the skin color of yellow to white appearance in color.

FIG. 8 shows how emitters (quantum dots or Fluorescent nanoparticles) change the yellow skin to white color. Sunlight illuminates emitters and the skin surface. By selecting emitter of "correct" size (around 1.9 nm in this case) and composition (CdSe), the blue color light, which is the complementary color of yellow, will be emitted. However, the yellow skin will reflect the yellow color light and absorb the others. The additive mixture of blue emitted light and yellow reflected light gives a white appearance of the skin.

Figure 9:
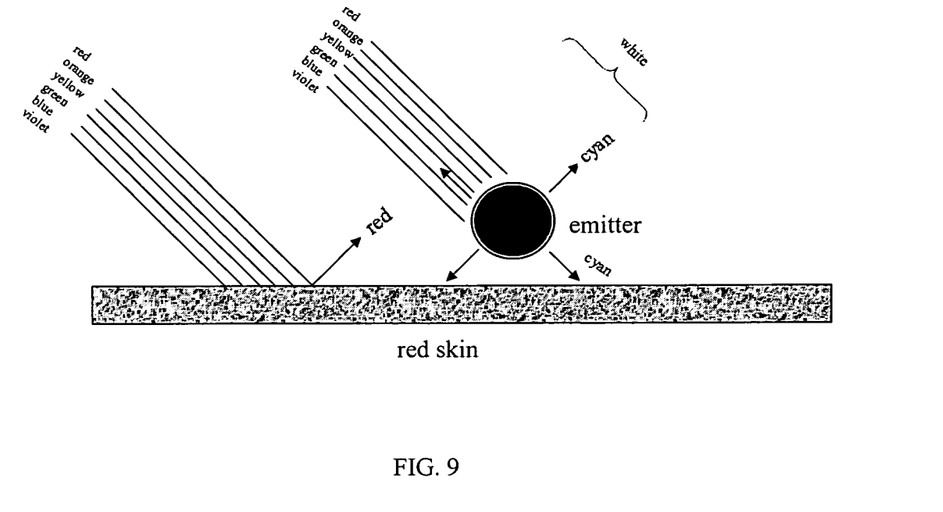
FIG. 9 is an enlarged view showing how a nanometer emitter changes the skin color of red to white appearance in color.

FIG. 9 shows how emitters change the red skin to white color. CdSe nanoparticles with diameter around 2.1 nm scatters the cyan light which is mixed with reflected red light from the skin giving a white appearance for red skin. Other compound alloy semiconductor particles can have similar properties of emission.

Figure 10:
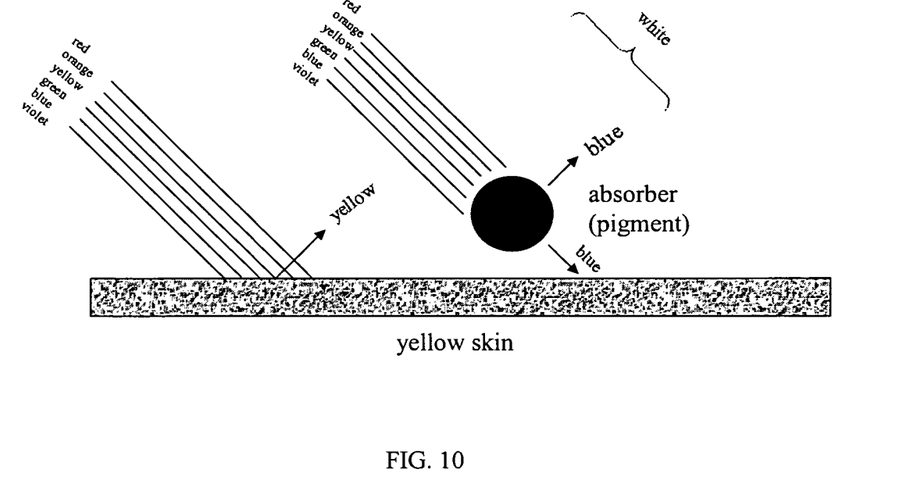
FIG. 10 is an enlarged view showing how a nanometer absorption pigment changes the skin color of yellow to white appearance in color.
Figure 11:
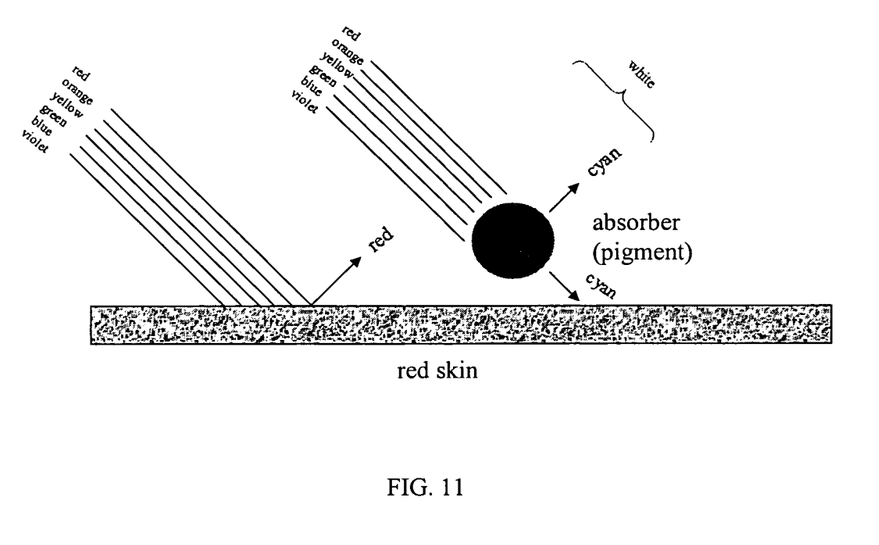
FIG. 11 is an enlarged view showing how a nanometer absorption pigment changes the skin color of red to white appearance in color.

An absorption particle can give a certain color by reflecting or transmitting certain wavelength and absorbing others. A color pigment is one kind of absorption particles. FIG. 10 shows how blue absorption pigments change the yellow skin to white color. The blue pigments reflect and transmit the blue color in the sunlight, the other colors in the illuminating sunlight are absorbed. The transmitted blue color is absorbed by the yellow skin. The reflected yellow light from the skin and reflected light from the pigments mix together to give a white appearance in skin color. FIG. 11 shows how cyan absorption pigments change the red skin to white color.

A metal nanoparticle is another kind of absorber which can be used to change the color efficiently. At small sizes, electrons at the surface of the nanoparticles slosh back and forth in unison (surface plasmon resonance), absorbing some color of light and reflecting off the particles certain wavelength. The reflected wavelength from metal nanoparticle depends on the size of the particle. For example, a 40 nm sphere reflecting the blue, a 25 nm gold sphere reflects the red light, however, a 100 nm gold sphere reflects the yellow light. Scientists today can make nanoparticles of many different shapes and sizes, actually you can get every color of the spectrum from metal nanoparticles.

Figure 12:
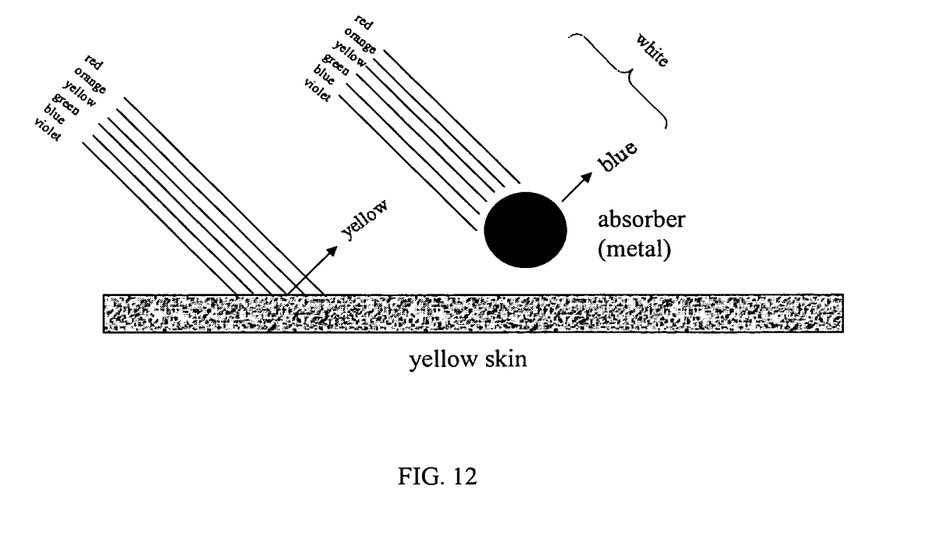
FIG. 12 is an enlarged view showing how metallic nanoparticles on skin changes the skin color of yellow to white appearance in color.
Figure 13:
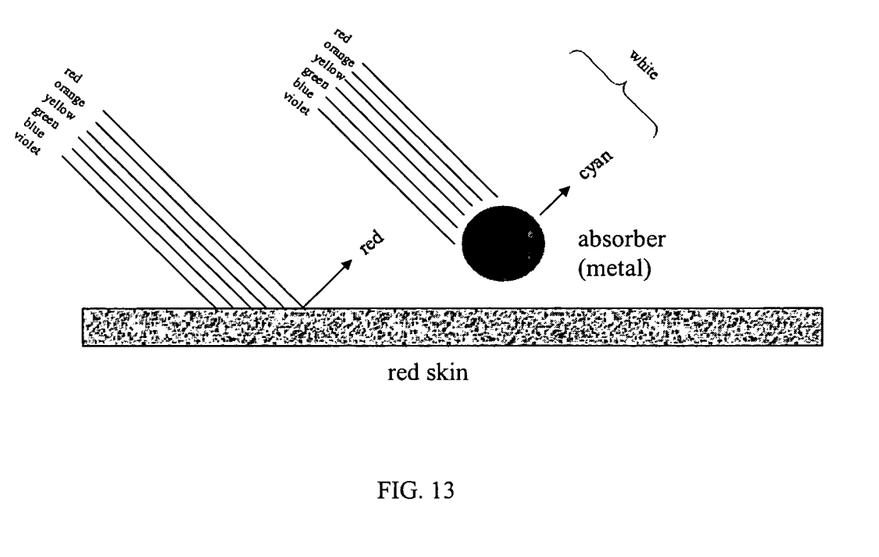
FIG. 13 is an enlarged view showing how metallic nanoparticle on skin changes the skin color of red to white appearance in color.

Small amounts of a metal nanoparticle applied to the skin can change the skin color significantly. FIG. 12 shows how metal nanoparticles change the yellow skin to white appearance in color. Certain size of metal nanoparticles, for example silver sphere of 40 nm, can reflect the blue light while absorbing the other colors. The additive mixture of the reflected blue color from the silver nanoparticles and reflected yellow color from the skin will present a white appearance of the skin. FIG. 13 shows how metal nanoparticles change the red skin to white color.

Nanoparticles can penetrate skin to last longer in the skin giving color enhancement.

From the foregoing description it can be seen that this invention makes available novel methods to change the color of skin for the application in cosmetics. The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed:

1. A method of changing the color perception of skin color comprising the steps of:
    establishing a first color corresponding to a skin color;
    determining a second perceived skin color desired to be attained;
    blending into a cosmetic composition to be applied to the skin micro-particles or nanoparticles consisting of metals or semi-conductor particles having physical and optical properties selected to optimize at least one of scattering and/or emission to provide a third color which when combined with said first color generates the perception that the skin color corresponds to the second color; and
    applying the composition directly to the skin having said skin first color.

2. The method as claimed in claim 1, wherein said the particles are selected from the group consisting of ZnO, $TiO_2$, MgO, CdSe, GaP, AlAs, InN, InP, AlSb, CdTe, ZnTe, BeTe, CdSe/ZnS, CdTe/CdS and ZnCdSe.

3. The method as claimed in claim 2, wherein the particle size is chosen to provide said third color which is a complimentary color to said second color that corresponds to the skin color to whiten the skin color perception.

4. The method as claimed in claim 3, wherein said complimentary color is blue for yellow skin to make the face appear whiter.

5. The method as claimed in claim 3, wherein the complimentary color is cyan (blue+green) for red skin to make the face appear whiter.

6. The method as claimed in claim 2, wherein said cosmetic composition is chosen to provide a complimentary color of the skin color to whiten the skin color perception.

7. The method as claimed in claim 6, wherein said the particles size and composition are chosen to emit light of the complimentary color for the skin color.

8. The method as claimed in claim 7, wherein said complimentary color is blue for yellow skin to make the face a appear whiter.

9. The method as claimed in claim 7, wherein the complimentary color is cyan (blue+green) for red skin to make the face appear whiter.

10. The method as claimed in claim 1, wherein the particles are fluorescent nanoparticles to give desired emission using a mixture of different sizes of particles.

11. The method as claimed in claim 10, wherein the particles are chosen to emit light of the complimentary color for the skin color.

12. The method as claimed in claim 11, wherein the complimentary emission color is blue for yellow skin to make the face appear whiter.

13. The method as claimed in claim 11, wherein the complimentary emission color is cyan (blue+green) for red skin to make the face appear whiter.

14. The method as claimed in claim 1, wherein the particles are absorption pigments.

15. The method as claimed in claim 14, wherein said pigments are chosen to reflect the complimentary color of the skin color and absorb other colors.

16. The method as claimed in claim 15, wherein said complimentary color is blue for yellow skin to make the face appear whiter.

17. The method as claimed in claim 15, wherein the complimentary color is cyan (blue+green) for red skin to make the face appear whiter.

18. The method as claimed in claim 1, wherein the particles are metallic nanoparticles.

19. The method as claimed in claim 18, wherein the metallic nanoparticles are chosen to reflect the complimentary color of the skin color and absorb other colors.

20. The method as claimed in claim 19, wherein the complimentary color is blue for yellow skin to make the face appear whiter.

21. The method as claimed in claim 19, wherein the metallic particles are silver sphere nanoparticles around the diameter of 40 nm giving the emission of blue color.

22. The method as claimed in claim 19, wherein the complimentary color is cyan (blue+green) for red skin to make the face appear whiter.

23. The method as claimed in claim 19, wherein the metallic particles are the mixture of silver sphere nanoparticles around the diameter of 40 nm (blue) and gold sphere nanoparticles around the diameter of 50 nm (green) to give a whiter appearance to the skin.

24. The method as claimed in claim 1, to change skin tone from yellow to white by adding blue emitters and/or blue scattering particles.

25. The method as claimed in claim 1, to change skin tone of Rosacea (Redness) to white by adding blue and green emitters and/or scattering particles.

26. The method as claimed in claim 1, wherein particles are added into a lotion to disperse the composite system onto the skin or face of a person to change appearance of color from yellow to white, blue to white or red to white.

27. The method as claimed in claim 1, wherein the size and composition of the particles are chosen to darken the skin.

28. The method as claimed in claim 1, wherein the size and composition of the particles are chosen to alter the skin color perception.

29. The method as claimed in claim 1, where various particles sizes are used to give a specific second color for different ambient light.

30. A method of changing the color perception of a material comprising the steps of:
    establishing a first color corresponding to a color of the material;
    determining a second perceived color desired to be attained for the material;
    blending into a composition to be applied to the material micro-particles or nanoparticles consisting of metals or semi-conductor particles having physical and optical properties selected to provide at least one of scattering and/or emission to provide a third color which when combined with said first color generates the perception that the material color corresponds to the second color.

31. The method as claimed in claim 30, wherein the size and composition of the particles are chosen to change or alter the color perception of a surface of the material to which they are applied.

32. The method as claimed in claim 31, wherein the material is selected from the class consisting of automobile paint, house paint, glass color and nail polish.

33. A method of changing the color perception of a material comprising the steps of:
    establishing a first color corresponding to a color of the material;
    determining a second perceived color desired to be attained for the material;
    blending into the material microparticles or nanoparticles selected from the group consisting of consisting of metals or semi-conductor particles having physical and optical properties selected to provide at least one of scattering and/or emission to provide a third color which when combined with said first color generates the perception that the material color corresponds to the second color.

34. The method as claimed in claim 33, wherein said particles are selected from the group consisting of ZnO, MgO, $TiO_2$, CdSe, GaP, AlAs, InN, InP, AlSb, CdTe, ZnTe, BeTe, CdSe/ZnS, CdTe/CdS and ZnCdSe.

35. The method as claimed in claim 1, wherein said semiconductor particles are selected from the group consisting of quantum dots and fluorescent nanoparticles.

36. A method of changing the color perception of skin color comprising the steps of:
    establishing a first color corresponding to a skin color;
    determining a second perceived skin color desired to be attained;
    blending into a cosmetic composition to be applied to the skin micro-particles or nanoparticles consisting of metals or semi-conductor particles having physical and optical properties selected to promote absorption for emission to provide a third color which when combined with said first color generates the perception that the skin color corresponds to the second color.

37. The method as claimed in claim 36, wherein said semiconductor particles are selected from the group consisting of quantum dots and fluorescent nanoparticles.

* * * * *